United States Patent
Kuriyama et al.

(10) Patent No.: US 11,859,205 B2
(45) Date of Patent: Jan. 2, 2024

(54) MEDIUM FOR CULTURING STEM CELLS

(71) Applicant: AJINOMOTO CO., INC., Tokyo (JP)

(72) Inventors: Yoko Kuriyama, Kawasaki (JP); Sho Senda, Kawasaki (JP); Yumi Ando, Kawasaki (JP); Tomomi Yoshida, Kawasaki (JP); Haruna Sato, Kawasaki (JP); Daisuke Ejima, Kawasaki (JP); Takayoshi Fujii, Kawasaki (JP); Masayo Date, Kawasaki (JP); Manabu Kitazawa, Kawasaki (JP)

(73) Assignee: AJINOMOTO CO., INC., Tokyo (JP)

(*) Notice: Subject to any disclaimer, the term of this patent is extended or adjusted under 35 U.S.C. 154(b) by 436 days.

(21) Appl. No.: 16/898,844

(22) Filed: Jun. 11, 2020

(65) Prior Publication Data

US 2020/0370006 A1 Nov. 26, 2020

Related U.S. Application Data

(60) Division of application No. 14/953,132, filed on Nov. 27, 2015, now abandoned, which is a continuation of application No. PCT/JP2014/064497, filed on May 30, 2014.

(30) Foreign Application Priority Data

May 30, 2013 (JP) .................... 2013-114285

(51) Int. Cl.
| | |
|---|---|
| C12N 5/074 | (2010.01) |
| C12N 5/0735 | (2010.01) |
| C12N 5/071 | (2010.01) |
| C12N 5/00 | (2006.01) |

(52) U.S. Cl.
CPC ......... *C12N 5/0602* (2013.01); *C12N 5/0018* (2013.01); *C12N 5/0696* (2013.01); *C12N 5/0606* (2013.01); *C12N 2500/36* (2013.01); *C12N 2501/998* (2013.01)

(58) Field of Classification Search
None
See application file for complete search history.

(56) References Cited

U.S. PATENT DOCUMENTS

| | | |
|---|---|---|
| 7,923,245 B2 | 4/2011 | Furue et al. |
| 8,153,429 B2 | 4/2012 | Robins et al. |
| 8,211,699 B2 | 7/2012 | Robins et al. |
| 8,415,158 B2 | 4/2013 | Robins et al. |
| 8,658,352 B2 | 2/2014 | Robins et al. |
| 8,685,726 B2 | 4/2014 | Schulz et al. |
| 2008/0050817 A1 | 2/2008 | Furue et al. |
| 2008/0113433 A1 | 5/2008 | Robins et al. |
| 2008/0268534 A1 | 10/2008 | Robins et al. |
| 2012/0021513 A1 | 1/2012 | Schulz et al. |
| 2012/0214237 A1 | 8/2012 | Robins et al. |
| 2013/0029418 A1* | 1/2013 | Angel ............... A61P 17/00 435/375 |
| 2013/0236973 A1 | 9/2013 | Rezania |
| 2013/0280802 A1 | 10/2013 | Schulz et al. |
| 2013/0309708 A1 | 11/2013 | Robins et al. |
| 2013/0309768 A1 | 11/2013 | Furue et al. |
| 2013/0344602 A1 | 12/2013 | Angel |
| 2014/0154802 A1 | 6/2014 | Robins et al. |
| 2014/0186948 A1 | 7/2014 | Schulz et al. |
| 2014/0234966 A1 | 8/2014 | Merkel et al. |
| 2015/0329832 A1 | 11/2015 | Senda et al. |

FOREIGN PATENT DOCUMENTS

| | | |
|---|---|---|
| CN | 101121753 A | 2/2008 |
| EP | 1 698 690 A1 | 9/2006 |
| WO | WO 2005/063968 A1 | 7/2005 |
| WO | WO 2007/101130 A2 | 9/2007 |
| WO | WO 2008/007082 A2 | 1/2008 |
| WO | WO 2010/129294 A2 | 11/2010 |
| WO | WO 2011/067465 A1 | 6/2011 |
| WO | WO 2012/078153 A1 | 6/2012 |
| WO | WO 2012/104936 A1 | 8/2012 |
| WO | WO 2013/006675 A1 | 1/2013 |
| WO | WO 2013/134378 A1 | 9/2013 |
| WO | WO 2014/119219 A1 | 8/2014 |

OTHER PUBLICATIONS

Chen, RF. Removal of Fatty Acids from Serum Albumin by Charcoal Treatment. The Journal of Biological Chemstry, (242) 2:173-181, 1967. (Year: 1967).*

Jun Lu, et al., "Palmitate Causes Endoplasmic Reticulum Stress and Apoptosis in Human Mesenchymal Stem Cells: Prevention by AMPK Activator" Endocrinology, vol. 153(11), Nov. 2012, pp. 5275-5284.

Uri Ben-David, et al., "Selective Elimination of Human Pluripotent Stem Cells by an Oleate Synthesis Inhibitor Discovered in a High-Throughput Screen" Cell Stem Cell, vol. 12, Feb. 7, 2013, pp. 167-179.

"An effective method for defatting albumin using resin columns" Short Communications, Biochim. Biophys. Acta, vol. 221, 1970, pp. 376-378.

Rachel Cameron, et al., "The Removal of Model Viruses, Poliovirus type 1 and Canine Parvovirus, During the Purification of Human Albumin using Ion-exchange Chromatographic Procedures" Biologicals, vol. 25, 1997, pp. 391-401.

K. Tanaka, et al., "Purification of human albumin by the combination of the method of Cohn with liquid chromatography" Brazilian Journal of Medical and Biological Research, vol. 31, 1998, pp. 1383-1388.

Raymond F. Chen, "Removal of Fatty Acids from Serum Albumin by Charcoal Treatment" The Journal of Biological Chemistry, vol. 242, No. 2, Issue of Jan. 25, 1967, pp. 173-181.

(Continued)

*Primary Examiner* — Allison M Fox
*Assistant Examiner* — Alyssa G Weston
(74) *Attorney, Agent, or Firm* — Oblon, McClelland, Maier & Neustadt, L.L.P.

(57) ABSTRACT

Culture media, which contain albumin carrying a reduced amount of fatty acid, are useful for culturing stem cells.

6 Claims, 4 Drawing Sheets

(56) References Cited

OTHER PUBLICATIONS

Guokai Chen, et al., "Chemically defined conditions for human iPS cell derivation and culture" Nat Methods, vol. 8(5), 2011, 21 Pages.
Extended European Search Report dated Oct. 26, 2016 in Patent Application No. 14803369.9.
Search Report dated Sep. 30, 2016, in Singaporean Patent Application No. 11201509767U.
Written Opinion dated Sep. 30, 2016, in Singaporean Patent Application No. 11201509767U.
Combined Chinese Office Action and Search Report dated May 3, 2017 in Patent Application No. 201480030956.4 (with English translation of Categories of Cited Documents).
Japanese Office Action (dated Apr. 3, 2018) in Japanese Patent Application No. 2018-519973 (with English Translation).
Office Action in Japanese Patent Application 2015-519973 dated Apr. 3, 2018, with English Translation.
Office Action dated Nov. 27, 2018 in Japanese Patent Application No. 2015-519973, 6 pages (with English language translation).
Masayoshi Iio, et al., "Death of serum-free mouse embryo cells caused by transforming growth factor beta 1 and effects of nutritional factors", Cytotechnology, vol. 10, 1992, pp. 175-181.
Vincent et al. Hypoalbuminemia in Acute Illness: Is There a Rationale for Intervention? Annals of Surgery, vol. 237, No. 3, 319-334 © 2003 Lippincott Williams & Wilkins, Inc.
Basi et al. "Microalbuminuria in Type 2 Diabetes and Hypertension" Diabetes Care, vol. 31, Supplement 2, Feb. 2008.
Spector (May 1975 The Journal of Lipid Research, 16, 165-179).
Chen (~The Journal of Biological Chemistry vol. 242, No. 2, Issue of Jan. 25, pp. 173-181, 1967).

* cited by examiner

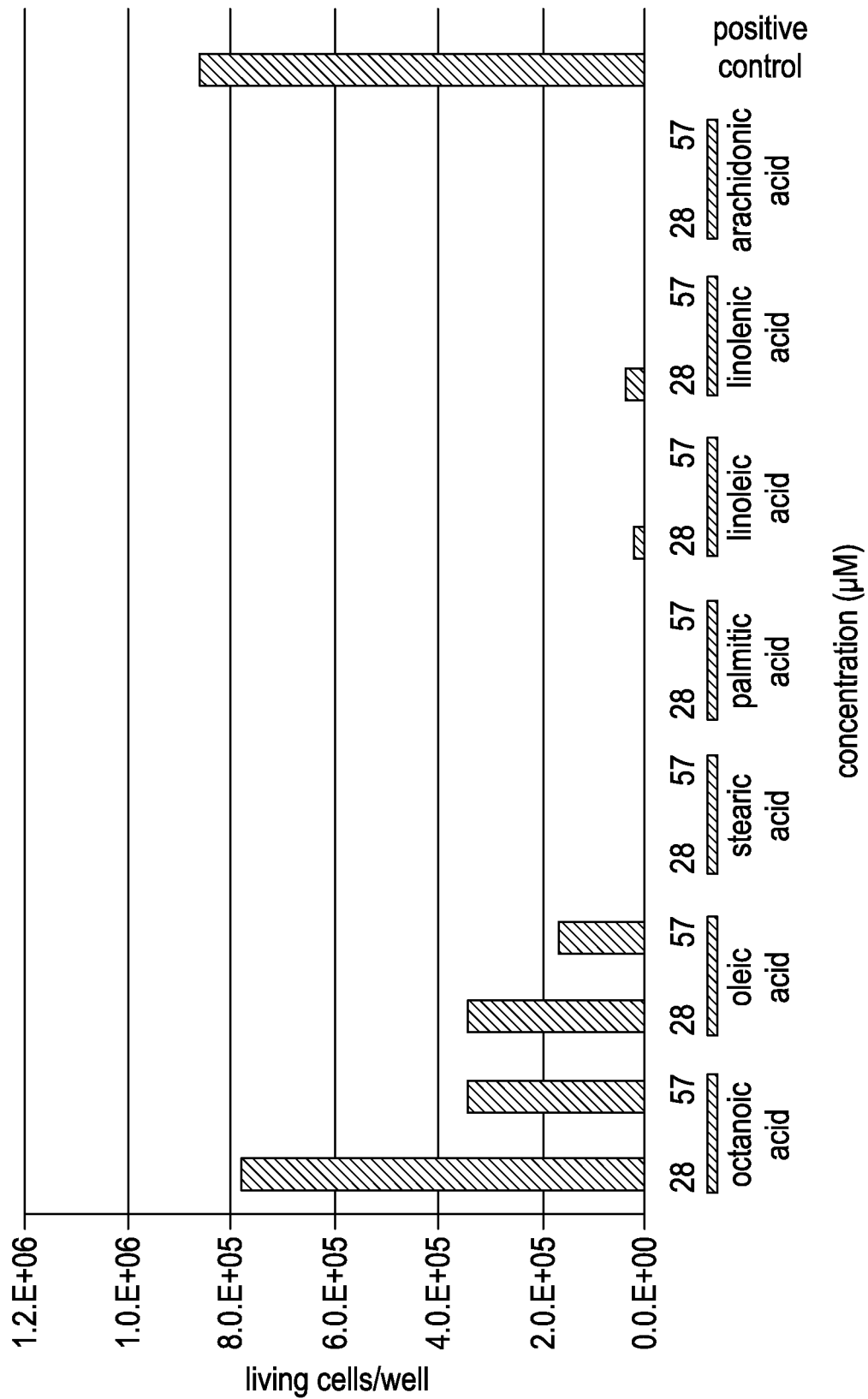

MEDIUM FOR CULTURING STEM CELLS

CROSS REFERENCES TO RELATED APPLICATIONS

This application is a divisional of U.S. patent application Ser. No. 14/953,132, filed Nov. 27, 2015, which is a continuation of International Patent Application No. PCT/JP2014/064497, filed on May 30, 2014, and claims priority to Japanese Patent Application No. 2013-114285, filed on May 30, 2013, all of which are incorporated herein by reference in their entireties.

BACKGROUND OF THE INVENTION

Field of the Invention

The present invention relates to media for culturing stem cells, method for producing such a medium, and the like.

Discussion of the Background

Conventionally, the culturing of stem cells (embryonic stem cells, induced pluripotent stem cells (iPS cell) and the like) has been conducted using a medium containing a serum. For example, fetal bovine serum (FBS) and the like are widely used for cell culture as an important additive for cell proliferation. However, when stem cells after such culturing are used for medical purposes, a xeno-derived component may become a source of infection with blood-borne pathogen or a xenoantigen. In addition, culture results may be inconsistent due to a difference between serum lots. Therefore, it has become mainstream in recent years to use a medium having a clear chemical composition (chemically-defined medium) for culturing stem cells, and the development of a serum-free medium is ongoing.

One of the highly important components for serum-free medium is albumin. Addition of albumin is expected to provide an effect of stably maintaining the medium property. Several kinds of albumin are commercially available for culturing cells. However, not all albumins provide an equivalent effect for cell culture, particularly the culture of stem cells, and the quality of albumin affects the culture results.

On the other hand, a treatment with activated carbon, ion exchange, heat treatment, and the like are known purification methods of albumin (see J. Biological Chemistry 1968, 212(2) 173-181; BioChim. Biophy. Acta 1970, 221, 376-378; Biologics 1997, 25, 391-401; and Brazilian journal of medicinal and biological research 1998, 31, 1383-1388, all of which are incorporated herein by reference in their entireties). Also, palmitic acid is reported to induce apoptosis of mesenchymal stem cells (see Endocrinology November 2012, 153(11), 5275-5284, which is incorporated herein by reference in its entirety), and there is a report that addition of a substance that inhibits oleic acid synthase in iPS cells results in accumulation of palmitic acid, which induces ER stress-apoptosis (see Cell Stem Cell 2013, 12, 167-179, which is incorporated herein by reference in its entirety).

WO 2013/006675, which is incorporated herein by reference in its entirety, describes that octanoic acid is used in a medium to stabilize albumin, and octanoic acid is harmful for culture of stem cells. However, use of a long chain fatty acid for stabilization of albumin is not described, nor are there any data or description showing that a long chain fatty acid is more harmful for culture of stem cells than octanoic acid which is a middle chain fatty acid, and exerts an adverse influence on the maintenance of undifferentiation potency. Also, WO 2013/134378, which is incorporated herein by reference in its entirety, describes that fatty acid-free albumin is contained in a medium for stem cells. This document does not describe how much fatty acid to be removed from albumin is sufficient for the cultivation of stem cells, and does not consider complication of removal of fatty acid from albumin since commercially available bovine serum-derived albumin manufactured by Proliant is used as fatty acid-free albumin.

SUMMARY OF THE INVENTION

Accordingly, it is one object of the present invention to provide novel novel media for culturing stem cells.

It is another object of the present invention to provide novel methods for preparing such a medium.

It is another object of the present invention to provide novel methods for culturing stem cells in such a medium.

It is another object of the present invention to elucidate the mechanism of inconsistent culture results due to the difference in the quality of albumin to be added to a medium.

It is another object of the present invention to provide media for culturing stem cells which show good culture results.

It is another object of the present invention to provide a method of producing media for culture.

It is another object of the present invention to provide a method of selecting albumin suitable for addition to a medium for culture.

It is another object of the present invention to provide a medium additive for media for culturing stem cells.

It is another object of the present invention to provide a culture system capable of maintaining stem cells in an undifferentiated state.

These and other objects, which will become apparent during the following detailed description, have been achieved by the inventors' discoveries of a correlation between a fatty acid carried by albumin to be added in culturing stem cells and cell proliferation that culture results can be improved by purification of albumin to remove fatty acid.

Accordingly, the present invention is as described below.

(1) A medium for culturing stem cells, comprising an albumin carrying a reduced amount of fatty acid.

(2) The medium of (1), wherein the reduction in the amount of fatty acid to be carried is achieved by a fatty acid removal treatment.

(3) The medium of (2), wherein the fatty acid removal treatment is a treatment with activated carbon.

(4) The medium of any of (1) to (3), wherein the amount of fatty acid carried by albumin is not more than 10 mg/g.

(5) The medium of any of (1) to (3), wherein the amount of fatty acid carried by albumin is not more than 6 mg/g.

(6) The medium of any of (1) to (3), wherein the amount of fatty acid carried by albumin is 0.1 mg/g to 0.65 mg/g.

(7) The medium of any of (1) to (6), wherein the content of fatty acid in the medium is not more than 60 μM.

(8) A medium for culturing stem cells, wherein the amount of fatty acid to be carried is 0.1 mg to 0.65 mg per 1 g albumin.

(9) The medium of (8), comprising not more than 60 μM of fatty acid.

(10) The medium of any of (1) to (9), wherein the fatty acid is a long chain fatty acid.

(11) The medium of any of (1) to (9), wherein the fatty acid is at least one kind selected from the group consisting of oleic acid, palmitic acid, stearic acid, linoleic acid, linolenic acid and arachidonic acid.

(12) The medium of any of (1) to (11), wherein the albumin is a human serum-derived albumin.

(13) The medium of any of (1) to (12), wherein the stem cell is a pluripotent stem cell.

(14) The medium of (13), wherein the pluripotent stem cell is an embryonic stem cell (ES cell) or an induced pluripotent stem cell (iPS cell).

(15) A method of culturing stem cells, comprising a step of cultivating in the medium of any of (1) to (12).

(16) The method of (15), wherein the stem cell is a pluripotent stem cell.

(17) The method of (16), wherein the pluripotent stem cell is an embryonic stem cell (ES cell) or an induced pluripotent stem cell (iPS cell).

(18) A method of selecting an albumin suitable for addition to a medium, comprising a step of measuring the amount of fatty acid carried, and selecting an albumin carrying a reduced amount of fatty acid.

(19) A method of producing a medium for culturing stem cells, comprising preparing an albumin carrying a reduced amount of fatty acid by a fatty acid removal treatment, and adding the prepared albumin to a medium.

(20) The method of (19), wherein the fatty acid removal treatment is a treatment with activated carbon.

(21) The method of (20), wherein the treatment with activated carbon is performed using 30 to 60 wt % of activated carbon relative to the weight of the albumin.

(22) The method of (20) or (21), wherein the treatment with activated carbon is performed at pH 6.7 to 7.3.

(23) The method of (20) or (21), wherein the treatment with activated carbon is performed at pH 3.7 to 4.3.

(24) The method of any of (19) to (23), wherein the amount of fatty acid carried by albumin is not more than 10 mg/g

(25) The method of any of (19) to (23), wherein the amount of fatty acid carried by albumin is not more than 6 mg/g.

(26) The method of any of (19) to (23), wherein the amount of fatty acid carried by albumin is 0.1 mg/g to 0.65 mg/g.

(27) The method of any of (19) to (26), wherein the content of fatty acid in the medium is not more than 60 µM.

(28) The method of any of (19) to (27), wherein the fatty acid is a long chain fatty acid.

(29) The method of any of (19) to (27), wherein the fatty acid is at least one kind selected from the group consisting of oleic acid, palmitic acid, stearic acid, linoleic acid, linolenic acid and arachidonic acid.

(30) The method of any of (19) to (29), wherein the albumin is human serum-derived albumin.

(31) The method of any of (19) to (30), wherein the stem cell is a pluripotent stem cell.

(32) The method of (31), wherein the pluripotent stem cell is an embryonic stem cell (ES cell) or an induced pluripotent stem cell (iPS cell).

(33) An additive for a medium for culturing stem cells, comprising an albumin carrying 0.1 mg/g to 0.65 mg/g of fatty acid.

(34) The additive of (33), wherein the fatty acid is a long chain fatty acid.

(35) The additive of (33), wherein the fatty acid is at least one kind selected from the group consisting of oleic acid, palmitic acid, stearic acid, linoleic acid, linolenic acid and arachidonic acid.

(36) The additive of any of (33) to (35), wherein the albumin is human serum-derived albumin.

(37) The additive of any of (33) to (36), wherein the stem cell is a pluripotent stem cell.

(38) The additive of (37), wherein the pluripotent stem cell is an embryonic stem cell (ES cell) or an induced pluripotent stem cell (iPS cell).

(39) A culture system of a stem cell, comprising a step of cultivating in a medium comprising an albumin carrying a reduced amount of fatty acid, wherein the amount of the fatty acid to be carried is so selected as to enable maintenance of the stem cell in an undifferentiated state.

(40) The culture system of (39), wherein the reduction in the amount of fatty acid is achieved by a fatty acid removal treatment.

(41) The culture system of (40), wherein the fatty acid removal treatment is a treatment with activated carbon.

(42) The culture system of any of (39) to (41), wherein the amount of fatty acid carried by albumin is not more than 10 mg/g.

(43) The culture system of any of (39) to (41), wherein the amount of fatty acid carried by albumin is not more than 6 mg/g.

(44) The culture system of any of (39) to (41), wherein the amount of fatty acid carried by albumin is 0.1 mg/g-0.65 mg/g.

(45) The culture system of any of (39) to (44), wherein the content of fatty acid in the medium is not more than 60 µM.

(46) The culture system of any of (39) to (45), wherein the fatty acid is a long chain fatty acid.

(47) The culture system of any of (39) to (45), wherein the fatty acid is at least one kind selected from the group consisting of oleic acid, palmitic acid, stearic acid, linoleic acid, linolenic acid and arachidonic acid.

(48) The culture system of any of (39) to (47), wherein the albumin is human serum-derived albumin.

(49) The culture system of any of (39) to (48), wherein the stem cell is a pluripotent stem cell.

(50) The culture system of (49), wherein the pluripotent stem cell is an embryonic stem cell (ES cell) or an induced pluripotent stem cell (iPS cell).

Effect of the Invention

Using the medium of the present invention, a stem cell can be grown while maintaining an undifferentiated state. Furthermore, using the medium of the present invention, a stem cell can be efficiently grown. Consequently, the frequency of medium exchange during culture can be reduced, and the cost of stem cell culture can be decreased.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 4 shows an influence of human serum-derived albumin re-carrying a different kind of fatty acid, on the growth of iPS cells.

DETAILED DESCRIPTION OF THE PREFERRED EMBODIMENTS

Figure 1:
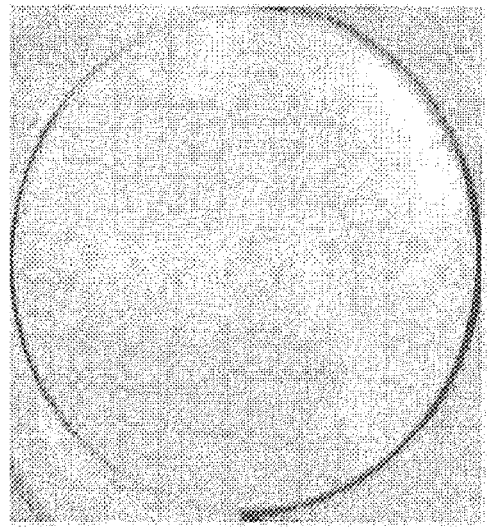
FIG. 1 shows culture results of stem cells in an albumin-added medium. The left Figure shows one embodiment of a culture dish marked with culture results + in Table 1, and the right Figure shows one embodiment of a culture dish marked with culture results −.
Figure 1:
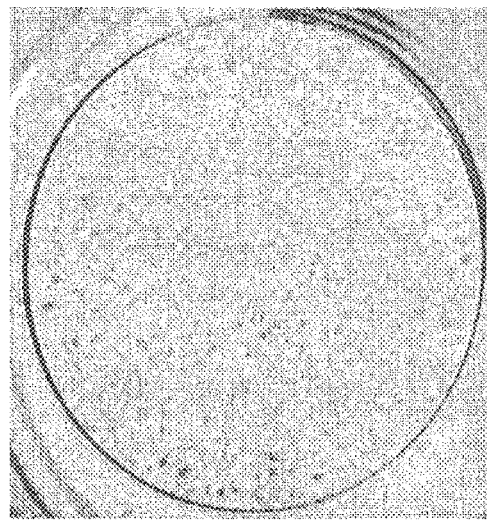

In the present invention, the term "stem cell" means an immature cell having self-renewal capacity and differentiation/proliferation capacity. The stem cell includes subpopulations such as pluripotent stem cell, multipotent stem cell, unipotent stem cell, and the like, according to the differentiation potency. The term pluripotent stem cell means a cell capable of differentiating into any tissue or cell constituting living organisms. The term multipotent stem cell means a cell capable of differentiating into plural, though not all, kinds of tissues and cells. The term unipotent stem cell means a cell capable of differentiating into particular tissues and cells.

Examples of pluripotent stem cells include embryonic stem cells (ES cell), embryonic germ cell (EG cell), induced pluripotent stem cell (iPS cell) and the like. It is preferably embryonic stem cells (ES cell) or an induced pluripotent stem cell (iPS cell). A stem cell established by cultivating an early embryo generated by nuclear transplantation of the nucleus of a somatic cell is also preferable as the pluripotent stem cell (see Nature, 385, 810 (1997); Science, 280, 1256 (1998); Nature Biotechnology, 17, 456 (1999); Nature, 394, 369 (1998); Nature Genetics, 22, 127 (1999); Proc. Natl. Acad. Sci. USA, 96, 14984 (1999); and Nature Genetics, 24, 109 (2000), all of which are incorporated herein by reference in their entireties). In addition, a pluripotent stem cell induced and selected by stress and stimulation on the cell is an example of the pluripotent stem cell.

Examples of multipotent stem cells include somatic stem cells such as mesenchymal stem cell, hematopoietic stem cell, neural stem cell, myeloid stem cell, germ line stem cell and the like, and the like. The multipotent stem cell is preferably a mesenchymal stem cell, more preferably a bone marrow mesenchymal stem cell. The mesenchymal stem cell broadly means a population of stem cells or progenitor cells thereof, which can differentiate into all or some of the mesenchymal cells such as osteoblast, chondroblast, lipoblast and the like.

As the basal medium to be used in the present invention, one known per se can be used depending on the kind of the stem cells, and is not particularly limited as long as it does not inhibit proliferation of the stem cells. Examples thereof include DMEM, EMEM, IMDM (Iscove's Modified Dulbecco's Medium), GMEM (Glasgow's MEM), RPMI-1640, α-MEM, Ham's Medium F-12, Ham's Medium F-10, Ham's Medium F12K, Medium 199, ATCC-CRCM30, DM-160, DM-201, BME, Fischer, McCoy's 5A, Leibovitz's L-15, RITC80-7, MCDB105, MCDB107, MCDB131, MCDB153, MCDB201, NCTC109, NCTC135, Waymouth's MB752/1, CMRL-1066, Williams' medium E, Brinster's BMOC-3 Medium, E8 medium (Nature Methods, 2011, 8, 424-429), ReproFF2 medium (ReproCELL Inc), a mixed medium thereof and the like. In addition, a medium altered for culture of stem cells, a mixture of the abovementioned basal medium and other medium, and the like may also be used.

The medium to be used in the present invention can contain an additive substance known per se. The additive substance is not particularly limited as long as it does not inhibit proliferation of stem cells. Examples thereof include growth factor (e.g., insulin etc.), iron source (e.g., transferrin etc.), polyamines (e.g., putrescine etc.), mineral (e.g., sodium selenate etc.), saccharides (e.g., glucose etc.), organic acid (e.g., pyruvic acid, lactic acid etc.), amino acid (e.g., L-glutamine), reducing agent (e.g., 2-mercaptoethanol), vitamins (e.g., ascorbic acid, d-biotin etc.), steroid (e.g., β-estradiol, progesterone etc.), antibiotic (e.g., streptomycin, penicillin, gentamicin etc.), buffering agent (e.g., HEPES etc.) and the like. In addition, additives that have been conventionally used for culturing stem cells can be contained as appropriate. The additive is preferably contained within a concentration range known per se.

The medium to be used in the present invention may contain a serum. Serum is not particularly limited as long as it is derived from an animal and does not inhibit the growth of stem cells. Preferred is a mammal-derived serum (e.g., fetal bovine serum, human serum etc.). The concentration of the serum may be any as long as it is within a concentration range known per se. However, a lower content of serum is more preferable, and the absence of serum is most preferable, since it is known that serum components also contain a differentiation factor of human ES cell, and the like, and the culture results may be inconsistent due to a difference between serum lots. Furthermore, when a stem cell after culture is used for medical purposes, a xeno-derived component may become an infection source of blood-mediated pathogen or a xenoantigen. Therefore, the absence of serum is preferable. When serum is not contained, a replacement additive of serum (e.g., Knockout Serum Replacement (KSR) (Invitrogen), Chemically-defined Lipid concentrated (Gibco), Glutamax (Gibco) etc.) may also be used.

The present invention provides a medium for culturing stem cells, which characteristically has a decreased fatty acid content (hereinafter to be also referred to as the medium of the present invention).

1. Medium of the Present Invention

While the medium of the present invention can be preferably used for proliferation of any stem cells, it is preferably used for proliferation of an embryonic stem cell or an induced pluripotent stem cell.

Also, the medium of the present invention can be preferably used for proliferation of stem cells derived from any animals. The stem cells cultured by using the medium of the present invention are, for example, pluripotent stem cells derived from rodents such as mouse, rat, hamster, guinea pig and the like, Lagomorpha such as rabbit and the like, Ungulata such as swine, bovine, goat, horse, sheep and the like, Carnivora such as dog, cat and the like, primates such as human, monkey, Macaca mulatta, marmoset, orangutan, chimpanzee and the like. Preferred are stem cells derived from human.

The medium of the present invention characteristically has a decreased fatty acid content. In one embodiment thereof, the medium of the present invention characteristically contains an albumin carrying a reduced amount of fatty acid. The albumin to be used in the present invention is not particularly limited as long as it is used for cell culture, and is directly added to a medium when the amount of fatty acid to be carried it already reduced, or added after a fatty acid removal treatment when the amount of fatty acid to be carried has not been reduced.

In the present specification, a fatty acid removal treatment of albumin is sometimes expressed as "purification" of albumin.

Examples of the fatty acid include saturated fatty acid having 8 to 20 carbon atoms (e.g., palmitic acid, stearic acid) and unsaturated fatty acid having 16 to 20 carbon atoms (e.g., oleic acid, linoleic acid, linolenic acid, arachidonic acid).

The present inventors studied to determine whether an influence on the growth of stem cells varies depending on the kind of fatty acid to be carried by albumin. As a result, they have found that long chain fatty acid shows a higher growth inhibitory action on stem cells than middle chain fatty acid. Therefore, in the medium of the present invention, long chain fatty acid is preferably reduced.

In the present specification, the term "long chain fatty acid" means a fatty acid having 12 or more carbon number. The long chain fatty acid to be reduced in the medium of the present invention is not particularly limited as long as it has an action to inhibit growth of stem cells. Specific examples of the long chain fatty acid to be reduced include oleic acid, stearic acid, palmitic acid, linoleic acid, linolenic acid and arachidonic acid. Preferable examples of the long chain fatty acid to be reduced include stearic acid, palmitic acid, linoleic acid, linolenic acid and arachidonic acid.

Specific examples of albumin include naturally-derived albumin such as ovalbumin, swine-derived albumin, bovine-derived albumin, human-derived albumin and the like, gene recombinant albumin such as bovine type, swine type, human type and the like, and the like. Particularly preferable examples thereof include serum-derived albumin and human type gene recombinant albumin (recombinant human albumin (rHSA)). Of these, human serum-derived albumin is particularly preferable.

Albumin is a protein having a high ability to bind to various substances, and binds to trace elements such as calcium, zinc and the like, fatty acid, enzyme, hormone and the like. For example, serum-derived albumin binds to various substances contained in serum. In the case of fatty acid, 1 molecule of albumin generally has an ability to bind to 2 molecules of fatty acid.

The fatty acid removal treatment of albumin is not particularly limited as long as it can reduce the amount of fatty acid carried by albumin, and a treatment with activated carbon (see J. Biological Chemistry 1968, 212(2), 173-181), an ion exchange treatment (see BioChim. Biophy. Acta 1970, 221, 376-378 and Biologics 1997, 25, 391-401), a heat treatment (see Brazilian journal of medicinal and biological research 1998, 31, 1383-1388) and the like can be mentioned. From the aspects of economic efficiency, convenience and the like, a treatment with activated carbon is preferable. The amount of fatty acid carried by albumin can be measured by a method generally practiced in the pertinent field, or a method analogous thereto. Examples thereof include methyl esterification of free fatty acid followed by detection by GC-MS, quantification by infrared spectroscopy and extraction method of Duncombe, ACS-ACOD method using acyl-CoA synthase (ACS) and acyl-CoA oxydase (ACOD) and the like. A commercially available measurement kit can be utilized for any of these.

The treatment with activated carbon may be performed under any conditions as long as a desired effect can be obtained. In one embodiment, the treatment with activated carbon can be performed using 30 to 60 wt %, preferably 40 to 50 wt %, of activated carbon per weight of albumin. While the pH of the treatment with activated carbon is not particularly limited as long as a desired effect can be obtained, it is pH 3 to 8, preferably pH 3.7 to 7.3, more preferably pH 3.7 to 4.3 or pH 6.7 to 7.3.

In one embodiment, a fatty acid removal treatment of albumin can also be preferably performed by ion exchange chromatography. A specific method thereof includes dialyzing an albumin solution against 40 mM sodium phosphate buffer adjusted to near neutral pH, subjecting same to anion exchange chromatography column (e.g., DEAE sepharose FF (GE Healthcare Japan)) previously equilibrated with the same buffer, then applying a linear concentration gradient to the 80 mM sodium phosphate adjusted to near neutral pH in a 10-fold volume of the column volume, whereby albumin fraction not bound to fatty acid can be recovered.

The amount of fatty acid carried by albumin in the present invention is reduced to a level at which stem cells can grow well. The amount of fatty acid carried by albumin when a fatty acid removal treatment is not performed is, for example, about 14 mg/g. The amount of fatty acid carried by albumin used in the present invention is preferably reduced to not more than 10 mg/g, more preferably not more than 6 mg/g, further more preferably substantially free of fatty acid. As used herein, "substantially free of fatty acid" means that albumin does not at all bind to fatty acid, or even if it does, it is less than the detection limit of the measurement method or measurement kit used for measuring the amount of fatty acid being carried.

When two or more kinds of fatty acids are bound to albumin, the total amount thereof is preferably reduced to fall within the above-mentioned range.

In one embodiment, the amount of fatty acid carried by albumin to be used in the medium of the present invention can be not more than 10 mg/g, more preferably not more than 6 mg/g and not less than 0.1 mg/g, based on the total weight of albumin. Specifically, the amount of fatty acid carried can be 0.1 mg/g to 0.8 mg/g, preferably 0.1 mg/g to 0.65 mg/g or 0.2 mg/g to 0.8 mg/g, more preferably 0.2 mg/g to 0.65 mg/g, most preferably 0.29 mg/g to 0.65 mg/g, based on the total weight of albumin. The amount of fatty acid to be carried is, for example, the amount of fatty acid carried by albumin which can be achieved by a fatty acid removal treatment of albumin performed by a convenient method such as a treatment with activated carbon and the like. When the amount of fatty acid to be carried is within the aforementioned range, the growth of stem cells can be promoted as compared to the use of a medium containing albumin without a fatty acid removal treatment. Therefore, the time, labor, cost and the like necessary for preparing a medium can be reduced, and the amount of fatty acid to be carried, which is within said range, can be preferably adopted for a convenient and large-scale production of the medium of the present invention.

While an amount of less than 0.1 mg/g of fatty acid carried by albumin can afford a desired effect, the amount of less than 0.1 mg/g of fatty acid to be carried requires, for example, a further fatty acid removal treatment by a method such as ion exchange chromatography and the like, thus requiring time, labor, cost and the like as compared to convenient methods such as a treatment with activated carbon and the like. Therefore, an amount of less than 0.1 mg/g of fatty acid carried by albumin is disadvantageous for a large-scale production of the medium of the present invention at an industrial level.

When two or more kinds of fatty acids are bound to albumin, the total amount thereof is preferably reduced to fall within the above-mentioned range.

In the present invention, while the amount of an albumin carrying a reduced amount of fatty acid to be added to a medium is not particularly limited as long as it is an amount generally added to a medium for cell culture, it is added to a basal medium for stem cell culture to a final concentration of 0 to 50 mg/mL, preferably 0.01 to 30 mg/mL, more preferably 0.05 to 10 mg/mL, further preferably 0.5 to 5 mg/mL, based on the total volume of the medium.

In another embodiment, the medium of the present invention has a reduced fatty acid content of the medium as a whole. As used herein, the "reduced fatty acid content of the medium as a whole" is intended to mean that not only the amount of fatty acid bound to albumin but also the amount of free fatty acid are reduced. In a preferable embodiment, the amount of fatty acid bound to albumin is reduced. The content of fatty acid in the medium is preferably not more than 60 μM, more preferably not more than 30 μM, further preferably not more than 10 μM, further more preferably not more than 9, 8, 7, 6, 5, 4, 3, 2 or 1 μM, based on the total volume of the medium, most preferably a concentration that does not exert a great influence on the concentration of fatty acid contained in the basal medium for culturing stem cells. The concentration of fatty acid contained in the basal medium for culturing stem cells is, for example, about 0.3 μM and 0.15 μM in commercially available Ham's Medium F-12 and DMEM/Ham's Medium F-12. Not exerting a great influence means remaining within 10-fold concentration change from the concentration of fatty acid contained in the basal medium for culturing stem cells. That is, not less than 0 μM, a concentration exceeding 0 μM, not less than 0.15 μM, not less than 0.3 μM, not less than 0.5 μM of fatty acid can be contained as long as it does not go beyond a 10-fold amount of the concentration of fatty acid contained in the basal medium for stem cell culture. The fatty acid content can be measured according to the above-mentioned method for measuring the amount of fatty acid bound to albumin, and a measurement kit is also commercially available.

When two or more kinds of fatty acids are contained in the medium, the total amount thereof is preferably reduced to fall within the above-mentioned range.

Examples of the fatty acid include saturated fatty acid having 8 to 20 carbon atoms (e.g., palmitic acid, stearic acid) and unsaturated fatty acid having 16 to 20 carbon atoms (e.g., oleic acid, linoleic acid, linolenic acid, arachidonic acid).

Based on the finding by the present inventors that long chain fatty acid shows a higher stem cell proliferation inhibitory action than middle chain fatty acid, in one embodiment, the fatty acid to be reduced is long chain fatty acid (fatty acid having 12 or more carbon atoms), and specific examples thereof include oleic acid, stearic acid, palmitic acid, linoleic acid, linolenic acid and arachidonic acid. Specific preferable examples include stearic acid, palmitic acid, linoleic acid, linolenic acid and arachidonic acid.

A medium for culturing stem cells, containing 0.1 mg to 0.65 mg of fatty acid to be carried per 1 g albumin is preferable. Furthermore, a medium for culturing stem cells, having a content of fatty acid in the medium of not more than 60 μM is preferable.

The present invention provides a method of producing a medium for culturing stem cells which characteristically has a reduced content of fatty acid (hereinafter to be also referred to as the production method of the present invention).

2. Production Method of the Present Invention

In one embodiment, the production method of the present invention includes preparing an albumin carrying a reduced amount of fatty acid by a fatty acid removal treatment (step 1), and adding the prepared albumin to a medium (step 2).

Step 1. Step of Preparing an Albumin Carrying a Reduced Amount of Fatty Acid by a Fatty Acid Removal Treatment It can be performed according to the above-mentioned section of "the medium of the present invention". In brief, human-derived serum albumin and rHSA are subjected to a fatty acid removal treatment such as a treatment with activated carbon, an ion exchange treatment, a heat treatment and the like (preferably treatment with activated carbon) to prepare an albumin carrying a reduced amount of fatty acid (preferably the amount of fatty acid to be carried is not more than 10 mg/g, more preferably not more than 6 mg/g, based on the total amount of albumin, and further preferably, substantially no fatty acid is carried). Reduction of the amount of fatty acid carried can be confirmed by measuring the amount of fatty acid bound to albumin by a method generally performed in the pertinent field or a method analogous thereto, and a commercially available measurement kit can be utilized.

In one embodiment, the amount of the fatty acid carried by albumin can be not more than 10 mg/g, more preferably not more than 6 mg/g, and not less than 0.1 mg/g, based on the total amount of albumin. Specifically, the amount of the fatty acid to be carried can be 0.1 mg/g to 0.8 mg/g, preferably 0.1 mg/g to 0.65 mg/g or 0.2 mg/g to 0.8 mg/g, more preferably 0.2 mg/g to 0.65 mg/g, most preferably 0.29 mg/g to 0.65 mg/g, based on the total amount of albumin.

Step 2. Step of Adding the Albumin Carrying a Reduced Amount of Fatty Acid Obtained in the Above-Mentioned Step 1 to a Medium It can be performed according to the above-mentioned section of "the medium of the present invention". An albumin carrying a reduced amount of fatty acid is added to a medium (basal medium) to a final concentration of 0 to 50 mg/mL, preferably 0.01 to 30 mg/mL, more preferably 0.05 to 10 mg/mL, further preferably 0.5 to 5 mg/mL, based on the total volume of the medium. As the basal medium, those exemplified in the above-mentioned section of "the medium of the present invention" can be similarly used.

In this way, a medium for culturing stem cells can be produced.

The present invention provides a method of selecting an albumin suitable for addition to a medium (hereinafter to be also referred to as the selection method of the present invention).

3. Selection Method of the Present Invention

In one embodiment, the selection method of the present invention is a method including measuring the amount of fatty acid carried by albumin (step 1), and selecting an albumin carrying a reduced amount of fatty acid (step 2).

Step 1. Step of Measuring the Amount of Fatty Acid Carried by Albumin

It can be performed according to the above-mentioned section of "the medium of the present invention". In brief, it can be performed by a method generally performed in the pertinent field or a method analogous thereto. Examples thereof include an extraction method of Duncombe, ACS-ACOD method using acyl-CoA synthase (ACS) and acyl-CoA oxydase (ACOD) and the like. A commercially available measurement kit can be utilized for any of these.

Step 2. Step of Selecting an Albumin Carrying a Reduced Amount of Fatty Acid

Based on the measurement results obtained in the above-mentioned step 1, an albumin carrying a reduced amount of fatty acid is selected. The "albumin carrying a reduced amount of fatty acid" is an albumin preferably carrying not more than 10 mg/g, more preferably not more than 6 mg/g, of fatty acid, based on the total amount of albumin, further preferably substantially no fatty acid carried.

In one embodiment, the amount of fatty acid carried by albumin can be not more than 10 mg/g, more preferably not more than 6 mg/g, and not less than 0.1 mg/g, based on the total amount of albumin. Specifically, the amount of fatty acid to be carried can be 0.1 mg/g to 0.8 mg/g, preferably 0.1 mg/g to 0.65 mg/g or 0.2 mg/g to 0.8 mg/g, more preferably 0.2 mg/g to 0.65 mg/g, most preferably 0.29 mg/g to 0.65 mg/g, based on the total amount of albumin.

The thus-selected "albumin carrying a reduced amount of fatty acid" is preferably added to a medium for culturing stem cells.

The present invention provides a method of culturing stem cells (hereinafter to be also referred to as the culture method of the present invention).

4. Culture Method of the Present Invention

The culture method of the present invention includes a step of cultivating stem cells in the medium of the present invention.

While a culture container to be used for the culture of stem cell is not particularly limited as long as stem cells can be cultured, a flask, tissue culture flask, dish, petri dish, tissue culture dish, multidish, microplate, microwell plate, multiplate, multiwell plate, microslide, chamber slide, Schale, tube, tray, culture bag, and roller bottle can be mentioned.

The culture container may be cell adhesive or cell non-adhesive, and is appropriately selected according to the object. A cell adhesive culture container may be coated with any cell supporting substrate such as extracellular matrix (ECM) and the like, in an attempt to improve the adhesiveness of the culture container surface to a cell. The cell supporting substrate may be any substance aiming at adhesion of stem cell or feeder cell (when used).

Other culture conditions can be appropriately determined. For example, while the culture temperature is not particularly limited, it can be about 30 to 40° C., preferably about 37° C. The $CO_2$ concentration can be about 1 to 10%, preferably about 2 to 5%. The oxygen partial pressure can be 1 to 10%.

5. Additive of the Present Invention

The present invention also provides an additive for a medium for culturing stem cells, which contains an albumin carrying a reduced amount of fatty acid (in the present specification, sometimes to be referred to as "the additive of the present invention").

The amount of fatty acid carried by albumin to be contained in the additive of the present invention is not more than 10 mg/g, more preferably not more than 6 mg/g, based on the total amount of albumin, and further preferably, substantially no fatty acid is contained. In one embodiment, the amount of fatty acid carried by albumin can be not more than 10 mg/g, more preferably not more than 6 mg/g, and not less than 0.1 mg/g, based on the total amount of albumin. Specifically, the amount of fatty acid to be carried can be 0.1 mg/g to 0.8 mg/g, preferably 0.1 mg/g to 0.65 mg/g, or 0.2 mg/g to 0.8 mg/g, more preferably 0.2 mg/g to 0.65 mg/g, most preferably 0.29 mg/g to 0.65 mg/g, based on the total amount of albumin.

The additive of the present invention can further contain an additive substance other than albumin as long as the desired effect is not impaired. The additive substance is not particularly limited as long as it does not inhibit proliferation of stem cells. Examples thereof include growth factor (e.g., insulin etc.), iron source (e.g., transferrin etc.), polyamines (e.g., putrescine etc.), mineral (e.g., sodium selenate etc.), saccharides (e.g., glucose etc.), organic acid (e.g., pyruvic acid, lactic acid etc.), amino acid (e.g., L-glutamine), reducing agent (e.g., 2-mercaptoethanol), vitamins (e.g., ascorbic acid, d-biotin etc.), steroid (e.g., β-estradiol, progesterone etc.), antibiotic (e.g., streptomycin, penicillin, gentamicin etc.), buffering agent (e.g., HEPES etc.) and the like. In addition, additive substance(s) that have been conventionally used for culturing stem cells can be contained as appropriate. The additive substance is preferably contained within a concentration range known per se.

The additive of the present invention may take any dosage form as long as the desired effect is obtained and, for example, solution, solid, powder and the like can be mentioned. When it is a solid or powder, it is dissolved in an appropriate buffer and the like to a desired concentration, and can be used.

The content of albumin carrying a reduced amount of fatty acid in the additive of the present invention is not particularly limited as long as the desired effect is obtained and, examples thereof include 0.05 to 250 mg/mL, preferably 0.05 to 150 mg/mL, more preferably 0.25 to 50 mg/mL, further preferably 2.5 to 25 mg/mL. The additive is added such that the final concentration of albumin in the medium is 0.01 to 50 mg/mL, preferably 0.01 to 30 mg/mL, more preferably 0.05 to 10 mg/mL, further preferably 0.5 to 5 mg/mL, based on the total volume of the medium, and can be preferably used for culturing stem cells.

The fatty acid that can be reduced in the additive of the present invention is as mentioned above, and the definition of stem cell in the additive of the present invention is also as mentioned above.

6. Culture System of the Present Invention

The present invention also provides a culture system of a stem cell, comprising a step of cultivating in a medium comprising an albumin carrying a reduced amount of fatty acid, wherein the amount of the fatty acid to be carried is so selected as to enable maintenance of the stem cell in an undifferentiated state (in the present specification, sometimes to be described as "the culture system of the present invention").

Being "so selected as to enable maintenance of the stem cell in an undifferentiated state" means that an amount of fatty acid to be carried which is within the range permitting growth of stem cell in an undifferentiated state is selected. In the culture system of the present invention, an amount of fatty acid to be carried which is within the range permitting that, preferably, the proportion of differentiated cells does not increase in the culture period, and stem cells are cultured while said proportion is maintained within about 10% at most, and more preferably, differentiated cells are not substantially mixed, stem cells are cultured in an undifferentiated state, and permitting growth of undifferentiated cells can be selected. The undifferentiated state of stem cells can be confirmed by a method known per se, and examples thereof include methods such as confirmation by alkaline phosphatase staining, confirmation of undifferentiated marker protein positive rate by FACS, confirmation of colony by a microscope and the like. In addition, cells judged by the method to be not in an undifferentiated state can be identified as differentiated cells.

The amount of fatty acid carried by albumin to be used for the culture system of the present invention is not particularly limited as long as it is reduced to an amount of fatty acid which is so selected as to enable maintenance of stem cells in an undifferentiated state. Examples thereof include an albumin carrying not more than 10 mg/g, more preferably not more than 6 mg/g, of fatty acid, based on the total amount of albumin, and still more preferably, an albumin carrying substantially no fatty acid. In one embodiment, the amount of fatty acid carried by albumin can be not more than 10 mg/g, more preferably not more than 6 mg/g, and not less than 0.1 mg/g, based on the total amount of albumin. Specifically, the amount of fatty acid to be carried can be 0.1 mg/g to 0.8 mg/g, preferably 0.1 mg/g to 0.65 mg/g or 0.2 mg/g to 0.8 mg/g, more preferably 0.2 mg/g to 0.65 mg/g, most preferably 0.29 mg/g to 0.65 mg/g, based on the total amount of albumin.

The fatty acid that can be reduced in the culture system of the present invention is as mentioned above, and the definition of stem cell in the culture system of the present invention is also as mentioned above.

Other features of the invention will become apparent in the course of the following descriptions of exemplary embodiments which are given for illustration of the invention and are not intended to be limiting thereof.

EXAMPLES

Materials and Methods

1. Purification of Albumin (Treatment with Activated Carbon)

To a solution (40 ml, 25%) of human serum albumin in saline was added phosphate buffer (pH 7.2, 40 ml), and the mixture was added to a phosphate buffer (20 ml) suspension of activated carbon (5 g, manufactured by Wako Pure Chemical Industries, Ltd.) previously heated at 200° C. for 30 minutes. After stirring at 4° C. for 3 hours, the mixture was centrifuged at 4° C., 11,900 rpm for 20 minutes. The activated carbon sediment was removed by decantation, and the reaction mixture was filtered through a 0.22 μm syringe filter. The filtered solution was diluted 100-fold, the absorbance was measured at wavelengths of 260 nm, 280 nm, 320 nm by UV absorption measuring apparatus UV1800 (manufactured by Shimadzu Corporation), and the concentration was calculated by calculation formula (A280-A320)/0.55× 100.

2. Cell Evaluation

Proliferative effect of various test compounds on induced pluripotent stem cell (iPS cell) was evaluated. As the iPS cell, 201B7 strain purchased from iPS Academia Japan, Inc. was used. Cell culture was performed under conditions of 5% $CO_2$/37° C. and using a culture vessel (Nippon Becton Dickinson Company, Ltd., Falconculture petri dish or Falconculture plate) coated with a basal membrane matrix.

Various test compounds were added at given concentrations to a medium of "E8" composition (disclosed in Nature Methods, 2011, 8, 424-429, which is incorporated herein by reference in its entirety) currently considered to be the minimum composition for cultivating human pluripotent stem cells, and used for culture, from which the effect was studied.

3. Measurement of the Amount of Fatty Acid Carried

A solution or powder corresponding to 10 mg of albumin was prepared to 200 μl with 1% brine, methanol (400 μl) and chloroform (200 μl) were added, and the mixture was shaken for 10 minutes. Chloroform (200 μl and 1% brine (200 μl) were added, the mixture was shaken for 10 min and centrifuged at 10,000 rpm for 2 minutes, and the bottom layer was collected. The solvent in the obtained chloroform layer was dried to solidness to give a sample for assay. The sample was dissolved in 2-propanol, and the amount of fatty acid was quantified based on oleic acid, by an analytical curve method and using a fatty acid measurement kit (LabAssay™ NEFA, manufactured by Wako Pure Chemical Industries, Ltd.). The absorbance was measured using SH900 (CORONA ELECTRIC Co., Ltd.).

Example 1. Influence of Various Albumins on Cell Culture

Human serum-derived albumin was added to a medium to a final concentration of 2.6 g/L, and the culture results of each albumin were compared. Several kinds of albumins were subjected to a purification treatment (fatty acid removal treatment) to remove lipid. The culture period was 1 week. 13,000 viable cells were seeded as single-cell per well of a 6-well plate. As a basal membrane matrix, a fragment containing an active domain of laminin 511, which was purchased from Osaka University, was applied at 5 μg/well. Y-27632 was added (final concentration 10 μM, NACALAI TESQUE, INC.: 08945-84) to a medium to be used for seeding. From the next day, the cells were cultured in a medium free of Y-27632.

The experiment was performed in triplicate for each medium and the results are shown in Table 1.

After the culture for 1 week, alkaline phosphatase (ALP) staining was performed to confirm maintenance of undifferentiation potency. For staining, alkaline phosphatase staining kit (Sigma-Aldrich Co. LLC.: 86-R) was used. FIG. 1 shows the state after culture of the cells marked with + or – in the column of culture results. When albumin obtained from each of Nova Biologics, Sigma, Biocell Laboratories was added to the medium, the cells did not proliferate except a part thereof. However, when the albumin after a purification treatment was added to the medium, the cells proliferated. In addition, the amount of fatty acid carried (fatty acid content) of all these albumins was measured to find the results shown in Table 1. From the above results, it was found that fatty acid bound to albumin inhibits normal cell proliferation.

TABLE 1

| albumin | derivation | purification | culture results | amount of fatty acid carried |
|---------|------------|--------------|-----------------|------------------------------|
| A | human serum | – | + | 0.5 |
| B | human serum | – | – | 14.9 |

TABLE 1-continued

| albumin | derivation | purification | culture results | amount of fatty acid carried |
|---|---|---|---|---|
| B | human serum | + | + | 1.4 |
| C | human serum | − | − | 14.6 |
| C | human serum | + | + | 2.2 | purification: treatment with activated carbon
amount of fatty acid carried (mg/g)

Example 2. Influence of Fatty Acid Re-Addition on Purified Human Serum-Derived Albumin Fatty Acid Addition Oleic acid (12.6 µl) was charged in a 15 ml falcon tube, and a solution of purified human serum albumin B (5.9 ml, 8.8%) was added. The solution was shaken at 37° C. for 3 hours, allowed to cool and filtered with a 0.22 µm syringe filter.

In this way, albumin adsorbed with oleic acid was obtained. Experiment was performed using a medium containing the obtained albumin adsorbed with oleic acid at a final concentration of 2.6 g/L (concentration of oleic acid in the medium 196 µM).

As for palmitic acid, stearic acid, linoleic acid, linolenic acid and arachidonic acid, a similar treatment was performed using the fatty acids at a dose described in Table 2 and purified human serum albumin to give albumin adsorbed with various fatty acids, and media added with albumin adsorbed with various fatty acids were prepared.

The amount of fatty acid carried by albumin was not measured after the above-mentioned adsorption operation.

Measurement of Fatty Acid Amount

A solution or powder corresponding to 10 mg of albumin was prepared to 200 µl with 1% brine, methanol (400 µl) and chloroform (200 µl) were added, and the mixture was shaken for 10 minutes. Chloroform (200 µl) and 1% brine (200 µl) were added, the mixture was shaken for 10 minutes and centrifuged at 10,000 rpm for 2 minutes, and the bottom layer was collected. The solvent in the obtained chloroform layer was dried to solidness to give a sample for assay. The sample was dissolved in 2-propanol, and the amount of fatty acid was quantified based on oleic acid, by an analytical curve method and using a fatty acid measurement kit (LabAssay™ NEFA, manufactured by Wako Pure Chemical Industries, Ltd.). The absorbance was measured using SH900 (CORONA ELECTRIC Co., Ltd.).

The fatty acids added to the media, concentration of fatty acids added, and the content of fatty acid per 1 g albumin (amount of fatty acid carried) are shown in Table 2.

TABLE 2

| albumin | fatty acid added | addition concentration (µM) | amount of fatty acid carried |
|---|---|---|---|
| B | oleic acid | 196 | 18.6 |
| B | oleic acid | 59 | 6.8 |
| B | oleic acid | 20 | 2.8 |
| B | oleic acid | 60 | 6.1 |
| B | oleic acid | 200 | 10.9 |
| B | palmitic acid | 20 | 1.3 |
| B | palmitic acid | 60 | 5.5 |
| B | palmitic acid | 200 | 12.1 |
| B | stearic acid | 200 | 12.1 |
| B | linoleic acid | 200 | 15.3 |
| B | linolenic acid | 200 | 23.6 |
| B | arachidonic acid | 200 | 14 | amount of fatty acid carried (mg/g)

Cell Evaluation

Using a medium containing, at the concentration indicated in Table 2, an albumin adsorbed with fatty acid, stem cells were cultured. The culture period was 1 week. 13,000 viable cells were single-cell seeded per well of a 6-well plate. As a basal membrane matrix, a fragment containing an active domain of laminin 511, which was purchased from Osaka University, was applied at 5 µg/well. Y-27632 was added (final concentration 10 µM) to a medium to be used for seeding. From the next day, the cells were cultured in a medium free of Y-27632.

Figure 2:
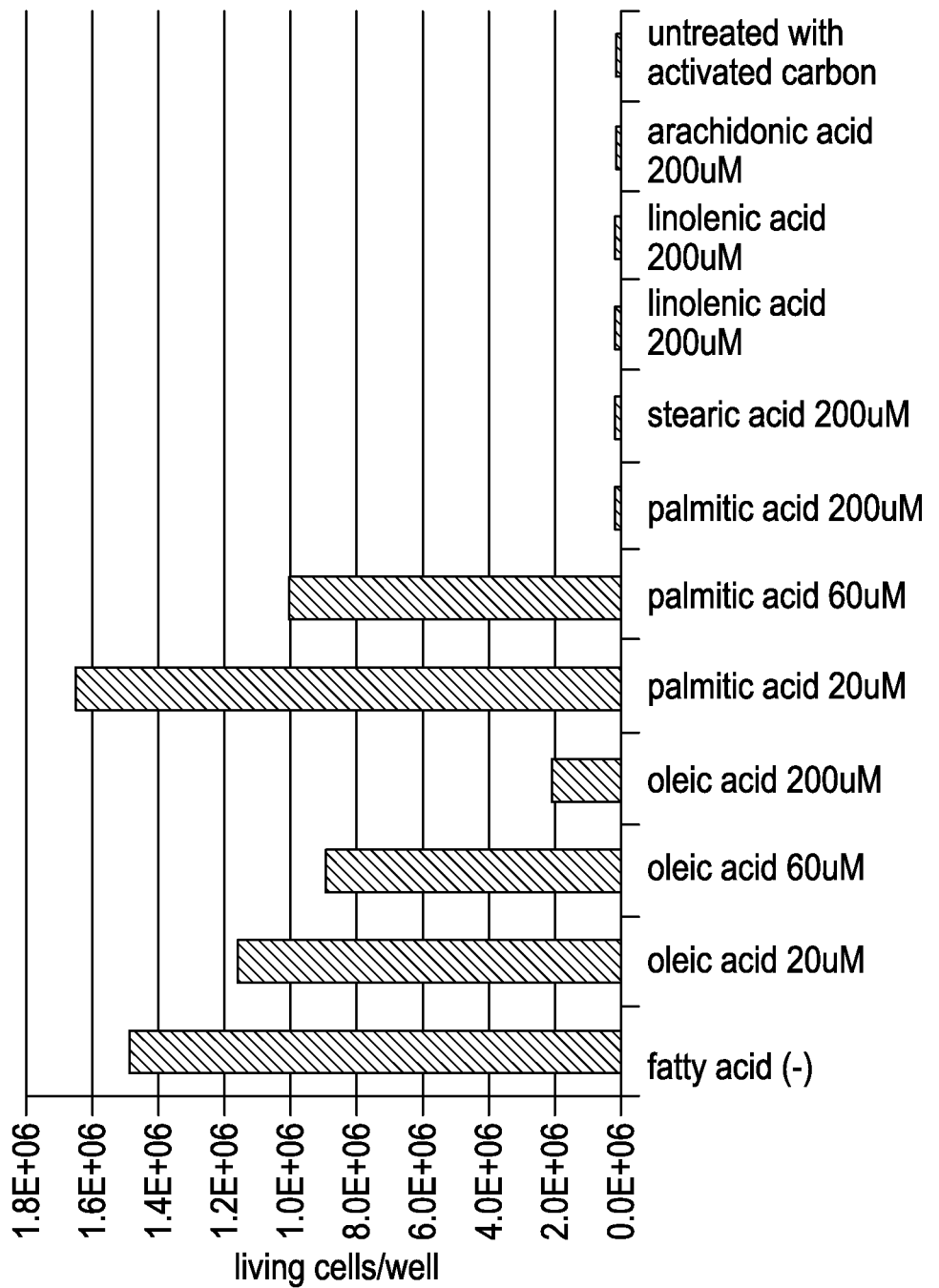
FIG. 2 shows measurement results of viable cell number when stem cells are cultured in a medium added with albumin adsorbing fatty acid.

The cells were detached from each well by TrypLE Select (Life Technologies: 12563-011), and the number of viable cells in the well was measured. The results are shown in FIG. 2. Addition of oleic acid and palmitic acid was found to suppress cell proliferation. The suppressive effect was in proportion to the concentration of fatty acid added, and addition of a high concentration of fatty acid resulted in stronger suppression of cell proliferation. From the above-mentioned results, it was found that cell culture efficiency decreases in a manner dependent on the concentration of fatty acid adsorbed to albumin.

Figure 3:
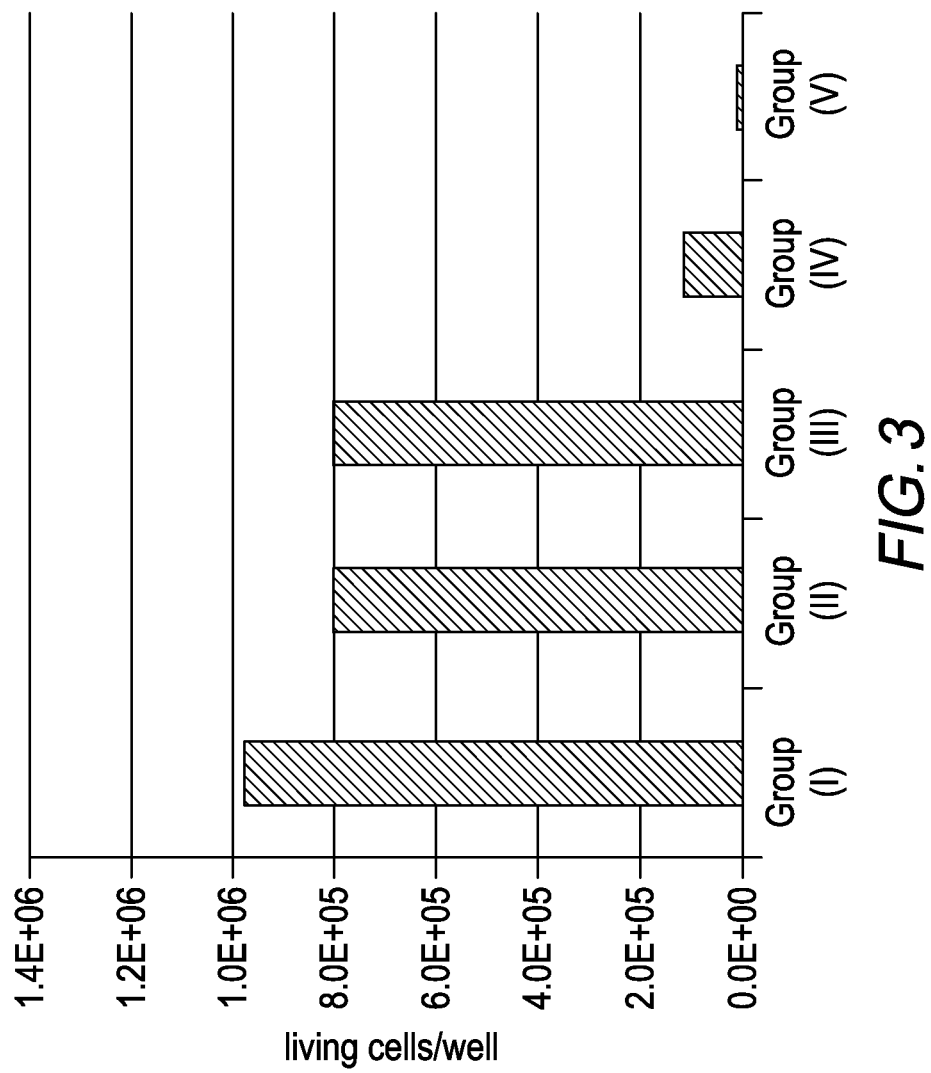
FIG. 3 shows an influence of human serum-derived albumin at varying purification degrees on the growth of iPS cells.

Example 3. Influence of Human Serum-Derived Albumin With Varying Purification Level on iPS Cell (FIG. 3)

Human serum albumins with the following five purification levels were prepared.

Group (I): Human serum albumin (Sigma) treated by a fatty acid removal treatment. The amount of fatty acid carried is considered to be not more than 0.07 mg/g.

Group (II): Human serum-derived albumin (NOVA Biologics, INC.) was used after purifying with 50 wt % of activated carbon relative to the weight of albumin at pH 4. The measurement result of the amount of fatty acid carried was 0.29 mg/g.

Group (III): Human serum-derived albumin (NOVA Biologics, INC.) was used after purifying with 50 wt % of activated carbon relative to the weight of albumin at pH 7. The measurement result of the amount of fatty acid carried was 0.65 mg/g.

Group (IV): Human serum-derived albumin (NOVA Biologics, INC.) was used after purifying with 25 wt % of activated carbon relative to the weight of albumin at pH 7. The measurement result of the amount of fatty acid carried was 0.92 mg/g.

Group (V): Human serum-derived albumin (NOVA Biologics, INC.) was used after purifying with 13 wt % of activated carbon relative to the weight of albumin at pH 7. The measurement result of the amount of fatty acid carried was 1.86 mg/g.

Each above-mentioned group of human serum albumin was added to a medium at a final concentration of 2.6 g/L, and iPS cells were cultured. A 6-well plate coated with a fragment containing an active domain of laminin 511 at 5 µg/well (iMatrix-511 (Nippi, Incorporated)) as a basal membrane matrix was used. iPS cells were single-cell seeded at 13,000 cells/well and cultured for 1 week. Y-27632 (NACALAI TESQUE, INC.: 08945-84) was added at a final concentration of 10 µM only to a medium to be used for seeding.

The cells were detached from each well by TrypLE Select (Life Technologies: 12563-011), and the number of viable cells was measured. FIG. 3 shows mean of three independent experiments for each group. When medium performance is free of problems, the number of viable iPS cells becomes not less than about $3.0 \times 10^5$ cells when cultured for one week by this culture method. As shown in FIG. 3, groups (I) to (III) showed good cell proliferation with a cell count exceeding $3.0 \times 10^5$. On the other hand, groups (IV) and (V) showed a clear growth inhibitory action. Therefrom it is clear that iPS cells can proliferate well at least when the amount of fatty acid carried by albumin is not more than 0.65 mg/g.

Groups (I) to (III) were further cultured for 1 week after the above-mentioned culture, and the differentiation rate was measured by alkaliphosphatase (ALP) staining. The differentiation rate (%) was calculated by ALP negative colony number/total colony number×100 of each well. The differentiation rates of groups (I), (II), and (III) were 0.4%, 1.5% and 2.6%, respectively. These numerical values can be said to be sufficiently low, which has demonstrated that all conditions are suitable for proliferating iPS cells while maintaining an undifferentiated state thereof. Similar results were also obtained by observation of colony under a microscope, and it was confirmed that a higher purification level of albumin leads to the maintenance of undifferentiated state of iPS cells at a higher rate.

Example 4. Influences of 7 Kinds of Purified Human Serum-Derived Albumins Re-Carrying Fatty Acid (FIG. 4)

Octanoic acid (18.3 µL) was charged in a 50 mL falcone tube, and a human serum albumin solution B (15 mL, 10%, Sigma) after a fatty acid removal treatment was added. The solution was shaken at 37° C. for 7 hours, left standing at 4° C. overnight, and filtered with a 0.22 µm syringe filter. In this way, an albumin re-adsorbed with octanoic acid was obtained. The amount of fatty acid carried by albumin re-adsorbed with octanoic acid was measured, and the albumin after re-adsorption with octanoic acid and a purified albumin before re-adsorption and after a fatty acid removal treatment were appropriately mixed while adjusting the ratio such that the final concentration of octanoic acid in the medium was 28 µM or 57 µM. The mixture was added to a medium such that the final concentration of albumin was 2.6 g/L.

As for oleic acid, stearic acid, palmitic acid, linoleic acid, linolenic acid and arachidonic acid, re-adsorption of fatty acid was performed in the same manner. The final concentration in and the amount of addition to the medium are also the same.

Using the medium produced as mentioned above, the influence of each fatty acid on the proliferation of iPS cells was studied. A 6-well plate coated with a fragment containing an active domain of laminin 511 at 5 µg/well (iMatrix-511 (Nippi, Incorporated)) as a basal membrane matrix was used. iPS cells were single-cell seeded at 13,000 cells/well and cultured for 1 week. Y-27632 (NACALAI TESQUE, INC.: 08945-84) was added at a final concentration of 10 µM only to a medium to be used for seeding. As a positive control, iPS cells were cultured using an albumin free of re-adsorption of fatty acid, i.e., albumin after a fatty acid removal treatment.

The cells were detached from each well by TrypLE Select (Life Technologies: 12563-011), and the number of the viable cells was measured. FIG. 4 shows mean of three independent experiments for each group.

When stearic acid, palmitic acid and arachidonic acid were re-adsorbed, the cells died at both 28 µM and 57 µM, and viable cells could not be obtained. Linoleic acid and linolenic acid had a strong proliferation inhibitory action on iPS cells, and the cells died by re-adsorption at 57 µM, and the proliferation of iPS cells was markedly suppressed even by re-adsorption at 28 µM, as compared to the positive control. Even when oleic acid was re-adsorbed, a concentration-dependent cell proliferation inhibitory action was found, and the number of viable cells was smaller than that of the positive control for both 28 µM and 57 µM. In the case of octanoic acid, however, a certain cell proliferation inhibitory action was found by re-adsorption at 57 µM, but the number of viable cells was equivalent to that of the positive control by re-adsorption at 28 µM. From these studies, it was demonstrated that when oleic acid, stearic acid, palmitic acid, linoleic acid, linolenic acid or arachidonic acid is re-adsorbed to albumin, the albumin shows an inhibitory action on the proliferation of iPS cells, irrespective of the concentration of addition. When octanoic acid is re-adsorbed, it was demonstrated that the number of viable cells is equivalent to that of the positive control depending on the concentration of re-adsorption, and the inhibitory action thereof is low.

From the above, it was shown that long chain fatty acids such as oleic acid and the like have strong toxicity to iPS cells and a high proliferation inhibitory action as compared to middle fatty acids such as octanoic acid and the like.

INDUSTRIAL APPLICABILITY

Using the medium of the present invention, stem cells can be proliferated while maintaining an undifferentiated state. Furthermore, using the medium of the present invention, stem cells can be efficiently proliferated, the frequency of exchange of culture medium can be reduced, and the culture cost of stem cells can be decreased.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of culturing for proliferation of a stem cell while maintaining an undifferentiated state, comprising:
    cultivating the stem cell in a medium comprising an albumin which comprises a reduced amount of long chain fatty acid; and
    maintaining a proportion of differentiated cells within 10% at most,
    wherein:
    said albumin is present in said medium in a concentration of 0.05 mg/mL to 10 mg/mL, based on the volume of said medium,
    and wherein said long chain fatty acid is at least one selected from the group consisting of oleic acid, palmitic acid, stearic acid, linoleic acid, linolenic acid, and arachidonic acid.

2. The method according to claim 1, wherein said stem cell is a pluripotent stem cell.

3. The method according to claim 2, wherein said pluripotent stem cell is an embryonic stem cell (ES cell) or an induced pluripotent stem cell (iPS cell).

4. The method according to claim 1, wherein said albumin is human serum-derived albumin.

5. The method according to claim 1, wherein a concentration of said each long chain fatty acid in said medium is less than 28 µM.

6. The method according to claim 1, wherein said albumin comprises fatty acid in an amount of 0.1 mg/g to 0.65 mg/g based on the total amount of said albumin, the amount of fatty acid being quantified based on oleic acid, by an analytical curve method using a fatty acid measurement kit.

* * * * *